United States Patent [19]
Zhou et al.

[11] Patent Number: 5,939,072
[45] Date of Patent: Aug. 17, 1999

[54] HERBAL COMPOSITION AND METHOD OF TREATING VIRAL INFECTION OF THE LIVER

[76] Inventors: James H. Zhou, 38 Blue Cliff Ter. #299, New Haven, Conn. 08513; Youwei Wang, North Rd 1, Guisan Hanyang Wuhan, China, 430050

[21] Appl. No.: 09/078,144

[22] Filed: May 13, 1998

[51] Int. Cl.⁶ .......................... A01N 65/00; A01N 43/04
[52] U.S. Cl. .................. 424/195.1; 514/54; 514/893; 514/894; 514/936
[58] Field of Search .................. 424/195.1; 514/54, 514/893, 894, 936

[56] References Cited

FOREIGN PATENT DOCUMENTS 1108509  12/1994  China .
53-033654  9/1978  Japan .
5117303  5/1993  Japan .

OTHER PUBLICATIONS

Hiroaki et al., Chem Pharm Bull, vol. 35, No. 3, pp. 1819–1827 (1987) Abstract Only.
Takashi et al., Shizuoka Daigaku Nogakubo Kenkyo Hokoku, vol. 36, pp. 77–83 (1986). Abstract Only.
Mizuno et al., Food Rev. Int, vol. 11, No. 1, pp. 69–81 (1995) Abstract Only.

*Primary Examiner*—James O. Wilson
*Attorney, Agent, or Firm*—Bachman & LaPointe, P.C.

[57] ABSTRACT

An herbal treatment composition includes a combination of mushroom derived polysaccharides wherein the polysaccharides are derived from at least two mushrooms from the group consisting of Maitake, Shiitake, Reishi, Poria, Cordyceps and Hericium.

18 Claims, No Drawings

HERBAL COMPOSITION AND METHOD OF TREATING VIRAL INFECTION OF THE LIVER

BACKGROUND OF THE INVENTION

The invention relates to an herbal composition and method for treating viral infections of the liver, specifically for treating Hepatitis B.

Hepatitis is a liver disorder which is manifested by various characteristics such as inflammation of the liver, fatigue and Hepatoma (liver tumor). The cause of the disorder is found to be associated with liver damage caused by viral infection or auto-immune response. Hepatitis B viral infection is one of the major causes of Hepatitis. There are approximately 300 million cases of Hepatitis B viral infection worldwide, and no cure of the infection is currently known. Interferon, which is a molecule released for none specific immune response, and anti-Hepatitis B immune ribonucleic acid (iRNA) are currently prescribed as therapy for Hepatitis B, and do show some effect in reduction of viral replication. However, iRNA treatment may be accompanied by undesirable side effects and health risks.

Thus, the need remains for more effective treatments for viral infections of the liver such as Hepatitis B and the like.

In light of the foregoing, it is the primary object of the present invention to provide a composition and method for treating viral infections of the liver.

It is a further object of the present invention to provide a composition and method for treating Hepatitis B.

It is a still further object of the present invention to provide a method for treating viral infections of the liver wherein treatment is simple and accompanied by little or no side effects.

Other objects and advantages of the present invention appear herein below.

SUMMARY OF THE INVENTION

In accordance with the present invention, the foregoing objects and advantages have been readily attained.

According to the invention, an herbal treatment composition is provided which comprises a combination of mushroom derived polysaccharides wherein said polysaccharides are derived from at least two mushrooms from the group consisting of Maitake, Shiitake, Reishi, Poria, Cordyceps and Hericium. Preferably, the composition includes polysaccharides derived from a combination of Maitake, Reishi, Shiitake and Cordyceps.

In further accordance with the present invention, a method for treating viral infection of the liver is provided, which method comprises the steps of providing an herbal treatment composition comprising a combination of mushroom derived polysaccharides wherein said polysaccharides are derived from at least two mushrooms from the group consisting of Maitake, Shiitake, Reishi, Poria, Cordyceps and Hericium; and administering said composition to a mammal having a viral infection of the liver.

DETAILED DESCRIPTION

The invention relates to an herbal treatment composition and method for advantageous use in treating viral infections of the liver such as Hepatitis B and the like. As will be further set forth below, the herbal treatment composition may suitably be provided in the form of a liquid herbal concentrate, a dry powder or powdered herbal concentrate, capsule, tablets, topical sprays, creams, ointments and the like, which includes one or more ingredients which have been found to be desirable in accordance with the present invention.

In accordance with the present invention, it has been found that a combination of polysaccharides derived from certain mushrooms provides for excellent results in the treatment of liver-related viral infections.

An herbal treatment composition in accordance with the present invention preferably comprises a combination of mushroom-derived polysaccharides wherein the polysaccharides are derived from at least two mushrooms selected from the group consisting of Maitake, Shiitake, Reishi, Poria, Cordyceps, and Hericium. Preferably, the composition includes polysaccharides derived from a combination of Maitake, Reishi, Shiitake and Cordyceps. Mushrooms such as those discussed can be readily treated according to known processes so as to obtain derived polysaccharides which are characteristic of the starting mushroom.

In accordance with the present invention, it has been found that a combination of two or more types of polysaccharide from the mushrooms listed above is more effective in treating viral infection of the liver than is any single polysaccharide of the type mentioned alone. Most preferably, the herbal treatment composition of the present invention includes Maitake, Reishi, Shiitake and Cordyceps derived polysaccharides, ideally in relative proportions as set forth below:

Maitake—20–40% wt
Reishi—10–30% wt
Shiitake—15–35% wt
Cordyceps—15–35% wt.

According to the invention, the herbal treatment composition preferably includes the desired combination of mushroom-derived polysaccharides in effective amounts for treating Hepatitis B and other viral infections of the liver, and most preferably including polysaccharides in a concentration of at least about 10 mg per unit composition or dose, more preferably at least about 50 mg per unit composition or dose, and ideally at least about 100 mg per unit composition or dose. Of course, the preferred dosage is body-weight dependent, and the preferred doses listed are for an individual of about 140 lbs. in body weight.

The herbal treatment composition of the present invention is preferably administered in unit compositions or unit doses of between about 0.5–1.5 milliliters or grams, depending upon the form of the composition. Composition amounts are therefore referred to herein as weights per unit composition.

Specific polysaccharides derived from the above-mentioned mushrooms which are advantageous in combination in accordance with the present invention include chain molecule poly and oligosaccharide such as lectins, glucans, glycans, peptide/protein associated poly or oligosaccharide or glycans/glucans, and mixtures thereof. Chemically, the polysaccharides consist of glucose, arabinose, manose, xylose and galactone. The composition may include crude extract or other non-polysaccharide derivative of certain mushrooms, so long as the listed percentage of polysaccharides are present as identified above.

The herbal treatment composition of the present invention has been found to have excellent results in treating viral infection of the liver, and may also be useful for treating other disorders such as psoriasis or purpura, particularly in connection with methods which are the subject of a co-pending and commonly assigned pending patent application of the present inventors.

The composition of the present invention may suitably be administered to a mammalian patient either orally as a liquid or powder concentrate to be added to a liquid, or in pill, capsule or tablet form, or topically as a spray, cream, ointment or the like. For example, the treatment composition of the present invention may be provided in standardized formula containing the desired polysaccharides at a concentration of at least about 10 mg/g or ml, more preferably a concentration of at least about 50 mg/g or ml, and ideally at least about 100 mg/g or ml, and this standardized formula is preferably administered to a patient, for example in doses of 0.5–1.5 gram or milliliter dosages of formula, at least once per day. In accordance with the present invention, it has been found that such a regimen or treatment method advantageously provides for improvement in viral infection of the liver and related liver problems, and further does not appear to have any side effect or undesirable result.

The following clinical data shows the excellent results obtained using the herbal treatment composition in accordance with the present invention to treat humans suffering from the Hepatitis B viral infection.

EXAMPLE

This example sets forth a clinical study in connection wit the Hepatitis B viral infection. A test population of 85 people was provided, and each of these people was classified as having the Hepatitis B viral infection. The age of persons in the test population ranged from 3 to 51 years of age. Members of the test population had the disease for periods as short as one month to periods as long as 10 years. The majority (70%) of the test population had had the Hepatitis B viral infection for a period of 1–3 years. The patients of the test population were identified as positive for Hepatitis B viral infection using the Elisa immune test method to identify three specific antigens which are induced by the Hepatitis B virus, specifically, HBsAg, HBeAg and HBcAg. The existence of these three antigens indicates positive viral infection. For example, HBeAg is associated with the transcription activity of a viral genome, and positive indication of this antigen indicates active viral replication.

The testers were divided into three groups, specifically Group A to whom the composition of the present invention was administered in capsule form in a high dosage (Hd) of 100 milligrams per dose, and 3 dose(s) per day. Group B was administered a low dosage (Ld) of composition in accordance with the present invention, which included 50 milligrams per dose of polysaccharides, and which was administered 3 times per day. Finally, Group C was a positive control group and was treated using iRNA according to known methods.

The polysaccharide composition administered to Groups A and B in accordance with the present invention had the following specific polysaccharide composition:

Maitake—30% wt

Reishi—20% wt

Shiitake—25% wt

Cordyceps 25% wt

After three months (90 days) of treatment, serum was taken from the patients, and the standard Elisa immune test was used to measure the serum HBsAg, HBeAg, and HBcAg. Hepatitis B viral DNA copies were also evaluated using standard PCR methods. In addition, urine samples, liver function, gall bladder and other conditions were monitored and recorded every 15 days.

Table 1 set forth below illustrates the percentage of patients who were tested as negative for the HBeAg, HBsAg, and HBcAg antigens after treatment as described.

TABLE 1

|  | A(Hd) | B(Ld) | Positive Control (iRNA) |
|---|---|---|---|
| Total Negativity | 63.3% | 40.0% | 43.3% |
| Negativity in HBeAg | 35.7% | 14.8% | 36.6% |

As shown, the high dose composition of the present invention showed a 63.3% negativity in the number of patients suffering from Hepatitis B, and further showed comparable reduction to iRNA treatment in connection with reduction in presence of HBeAg antigen which is indicative of viral replication. Thus, the high dosage treatment of the present invention provided comparable reduction in viral replication to a conventional treatment method using iRNA, but provided for an additional 20% reduction in total Hepatitis antigens present, and the low dosage also provided a beneficial result. Furthermore, the results obtained using the composition of the present invention are not believed to be accompanied by any side effects. In contrast, studies have shown that iRNA can break down in the human body into nucleosides which could be a source of DNA mutation, thereby posing a risk of cancer or other genetic disorders. Further, iRNA treatment may affect nuclear metabolism.

In addition, other Hepatitis symptoms including fatigue and fullness or pain in the stomach disappeared and the level of serum amino transferase became normal during the treatment in accordance with the present invention.

It is also noted that three patients of the above group at the beginning of the test were also diagnosed as suffering from symptoms of psoriasis, and these symptoms also improved during the treatment in accordance with the present invention.

No obvious side effects were observed in Groups A and B, and no noticeable discomfort complaints were registered during or after treatment, and all liver, blood and urine examinations and ultrasound scanning showed normal after the treatment.

In related studies, it has been demonstrated, and it is believed, that the composition of the present invention serves to protect against liver damage by improving the immune system response to particular viral infections, for example by enhancing the engulfing function of microphages and also by preventing white blood cell decreases which could be caused by chemical toxicity.

This invention may be embodied in other forms or carried out in other ways without departing from the spirit or essential characteristics thereof. The present embodiment is therefore to be considered as in all respects illustrative and not restrictive, the scope of the invention being indicated by the appended claims, and all changes which come within the meaning and range of equivalency are intended to be embraced therein.

We claim:

1. An herbal treatment composition for treating viral infection, comprising a combination of mushroom derived polysaccharides wherein said polysaccharides are derived from at least two types of mushrooms selected from the group consisting of Maitake, Shiitake, Reishi, Poria, Cordyceps and Hericium.

2. A composition according to claim 1, wherein said polysaccharides are derived from at least two types of mushrooms selected from the group consisting of Maitake, Reishi, Shiitake, and Cordyceps.

3. A composition according to claim 1, wherein said polysaccharides are present in a concentration of at least about 10 mg per unit composition.

4. A composition according to claim 1, wherein said polysaccharides are present in a concentration of at least about 50 mg per unit composition.

5. A composition according to claim 1, wherein said polysaccharides are present in a concentration of at least about 100 mg per unit composition.

6. A composition according to claim 1, wherein said polysaccharides are derived from mushrooms comprising Maitake—20–40% wt; Reishi—10–30% wt; Shiitake—15–35% wt; and Cordyceps—15–35% wt.

7. A composition according to claim 1, wherein said composition is a liquid.

8. A composition according to claim 1, wherein said composition is a dry powder.

9. A method for treating Hepatitis B viral infections of the liver, comprising the steps of:
providing an herbal treatment composition comprising a combination of mushroom derived polysaccharides wherein said polysaccharides are derived from at least two types of mushrooms selected from the group consisting of Maitake, Shiitake, Reishi, Poria, Cordyceps and Hericium; and administering said composition in an effective anti Hepatitis B viral amount to a mammal having a Hepatitis B viral infection of the liver whereby viral replication is reduced.

10. A method according to claim 9, wherein said polysaccharides are derived from at least two mushrooms selected from the group consisting of Maitake, Reishi, Shiitake and Cordyceps.

11. A method according to claim 9, wherein said polysaccharides are present in a concentration of at least about 10 mg per unit composition.

12. A method according to claim 9, wherein said polysaccharides are present in a concentration of at least about 50 mg per unit composition.

13. A method according to claim 9, wherein said polysaccharides are present in a concentration of at least about 100 mg per unit composition.

14. A method according to claim 9, wherein said composition is a liquid.

15. A method according to claim 9, wherein said composition is a dry powder.

16. A composition according to claim 1, wherein said viral infection of the liver comprises Hepatitis B.

17. A method according to claim 9, wherein said administering step comprises administering one unit dose of said composition to said mammal per day, and wherein said unit dose contains a concentration of said polysaccharides of at least about 50 mg per unit dose.

18. A method according to claim 17, wherein said unit dose contains a concentration of said polysaccharides of at least about 100 mg per unit dose.

* * * * *